United States Patent
Geva et al.

(10) Patent No.: US 11,298,557 B2
(45) Date of Patent: Apr. 12, 2022

(54) METHOD AND SYSTEM FOR LOCATING A DEFIBRILLATOR

(71) Applicants: G-MEDICAL INNOVATIONS HOLDINGS LTD, Grand Cayman (KY); Zeev Rotstein, Rosh Ha'ain (IL)

(72) Inventors: Nir Geva, Ness Ziona (IL); Zeev Rotstein, Rosh Ha'ain (IL)

(*) Notice: Subject to any disclaimer, the term of this patent is extended or adjusted under 35 U.S.C. 154(b) by 13 days.

(21) Appl. No.: 16/484,125

(22) PCT Filed: Feb. 8, 2018

(86) PCT No.: PCT/IL2018/050146
§ 371 (c)(1),
(2) Date: Aug. 7, 2019

(87) PCT Pub. No.: WO2018/146680
PCT Pub. Date: Aug. 16, 2018

(65) Prior Publication Data
US 2020/0016419 A1    Jan. 16, 2020

Related U.S. Application Data

(60) Provisional application No. 62/457,185, filed on Feb. 10, 2017.

(51) Int. Cl.
*A61N 1/39*    (2006.01)
*G16H 40/67*    (2018.01)
*A61B 5/00*    (2006.01)

(52) U.S. Cl.
CPC .......... *A61N 1/3904* (2017.08); *A61B 5/7405* (2013.01); *A61B 5/747* (2013.01); *G16H 40/67* (2018.01); *A61B 5/743* (2013.01); *A61B 2560/0242* (2013.01); *A61N 1/3925* (2013.01); *A61N 1/3993* (2013.01)

(58) Field of Classification Search
CPC ........ A61N 1/39; A61N 1/3904; A61B 5/747; A61B 5/7405; A61B 2560/0242; G16H 40/67; G01N 29/2418; G10K 15/046
See application file for complete search history.

(56) References Cited

U.S. PATENT DOCUMENTS

| | | | | |
|---|---|---|---|---|
| 2003/0025602 A1* | 2/2003 | Medema | ................ | G16H 40/20 340/568.1 |
| 2012/0189140 A1* | 7/2012 | Hughes | .................. | H04M 3/56 381/123 |
| 2015/0110277 A1* | 4/2015 | Pidgeon | ................. | G08B 23/00 381/56 |
| 2016/0278652 A1* | 9/2016 | Kaib | ..................... | H04W 4/029 |

* cited by examiner

*Primary Examiner* — Carl H Layno
*Assistant Examiner* — Aya Ziad Bakkar
(74) *Attorney, Agent, or Firm* — Reches Patents

(57) ABSTRACT

A defibrillator that may include circuitry for supplying a dose of electric current to a heart of a patient; and a location device; wherein the location device comprises a controller for controlling the location device, a receiver for receiving a location request, and a location response unit for generating a location response; wherein the location response is indicative of a location of the defibrillator.

11 Claims, 7 Drawing Sheets

METHOD AND SYSTEM FOR LOCATING A DEFIBRILLATOR

CROSS REFERENCE

This applications claims priority from U.S. provisional patent 62/457,185 filing date Feb. 10, 2017

BACKGROUND

Defibrillation (www.wikipedia.org) is a treatment for life-threatening cardiac dysrhythmias, specifically ventricular fibrillation (VF) and non-perfusing ventricular tachycardia (VT).

A defibrillator delivers a dose of electric current (often called a countershock) to the heart. The electrical shock does not have to be timed with the heart's intrinsic cardiac cycle. This depolarizes a large amount of the heart muscle, ending the dysrhythmia. Subsequently, the body's natural pacemaker in the sinoatrial node of the heart is able to re-establish normal sinus rhythm.

Various countries require that a defibrillator will be installed in designated premises (such as schools, shopping malls, pools, sport facilities, and the like) that are accessed by members of the public.

Nevertheless, due to the cost of the defibrillator and the need to properly maintain and test the defibrillator, a single defibrillator may be allocated per a relatively large area.

When a life threatening cardiac event occurs the search for the nearest defibrillator can consume valuable time.

There is a growing need to provide efficient methods and systems for locating a defibrillator.

SUMMARY

There may be provided a defibrillator that may include circuitry for supplying a dose of electric current to a heart of a patient; and a location device; wherein the location device may include a controller for controlling the location device, a receiver for receiving a location request, and a location response unit for generating a location response; wherein the location response may be indicative of a location of the defibrillator.

The location response unit may be arranged to send a location response that may include instructions for finding the defibrillator.

The location response unit may be arranged to send a location response that may include an indication of the location of the defibrillator.

The location response unit may be arranged to send a location response that may include coordinates of the defibrillator.

The location response unit may be arranged to send a location response that may include a location of an object that may be nearby the defibrillator.

The location response unit may be arranged to generate a location response that may be perceivable to a human only within a predefined range from the defibrillator.

The predefined range may be ten meters.

The predefined range may be one hundred meters.

The location response unit may include a sensor for sensing an ambient condition; wherein the location response unit may be arranged to select the location response based on the ambient condition sensed by the sensor.

The ambient condition may be light.

The location response unit may be arranged to sense daylight that exceeds a threshold and to output an audio location response instead of a visual location response.

The location response unit may be arranged to sense daylight that exceeds a threshold and to output a location response that may be aimed to another device instead of a visual location response.

The location response unit may be arranged to change any parameter of the location response based on the ambient condition.

The location response unit may be arranged to change any parameter of the location response based on a time of the location request.

The location unit may be arranged to select a type of location response based on the ambient condition.

The ambient condition may be sound.

The location response unit may be arranged to sense noise that exceeds a threshold and to output a visual location response instead of an audio location response.

The location response unit may be arranged to sense noise that exceeds a threshold and to output a location response that may be aimed to another device instead of an audio location response.

The ambient condition may be electromagnetic interferences.

The location response unit may be arranged to sense electromagnetic interferences that exceeds a threshold and to output a visual location response instead of a location response that may be aimed to another device.

The location response unit may be arranged to sense electromagnetic interferences that exceeds a threshold and to output an audio location response instead of a location response that may be aimed to another device.

The defibrillator may be arranged to retrieve or receive health information about the patient; and to configure the circuitry according to the health information.

The receiver may be arranged to receive a location request that may include the health information.

The receiver may be arranged to receive a location request that may be not included in the health information.

The location response unit may be configured to transmit an alert to a predefined third party about an occurrence of a life threatening cardiac event of the patient.

The location response unit may be arranged to detect the location request by finding a dedicated sequence signal included in the location request.

The receiver may be arranged to receive the location request over a carrier frequency that may be allocated to an emergency service.

There may be provided a system that may include a defibrillator and a location device; wherein the defibrillator may include circuitry for supplying a dose of electric current to a heart of a patient; and wherein the location device may include a controller for controlling the location device, a receiver for receiving a location request, and a location response unit for generating a location response; wherein the location response may be indicative of a location of the defibrillator.

The defibrillator may be attached to the location device.

The location response unit may include a sensor for sensing an ambient condition; wherein the location response unit may be arranged to select the location response based on the ambient condition sensed by the sensor.

There may be provided a method for assisting in locating a defibrillator, the method may include receiving a location request, by a receiver of location device that may be associated with a defibrillator; and generating, by a location response unit of the location device, a location response that may be indicative of a location of the defibrillator, wherein the defibrillator may include circuitry for supplying a dose of electric current to a heart of a patient.

The method may include sending, by the location response unit, a location response that may include instructions for finding the defibrillator.

The method may include sending, by the location response unit, a location response that may include an indication of the location of the defibrillator.

The method may include sending, by the location response unit, a location response that may include coordinates of the defibrillator.

The method may include sending, by the location response unit, a location response that may include a location of an object that may be nearby the defibrillator.

The method may include generating, by the location response unit, a location response that may be perceivable to a human only within a predefined range from the defibrillator.

The predefined range may be ten meters.

The predefined range may be one hundred meters.

The method may include sensing, by a sensor of the location response unit, an ambient condition; and selecting, by the location response unit, the location response based on the ambient condition sensed by the sensor.

The ambient condition may be light.

The method may include sensing, by the location response unit, daylight that exceeds a threshold and outputting an audio location response instead of a visual location response.

The method may include sensing, by the location response unit, daylight that exceeds a threshold and outputting a location response that may be aimed to another device instead of a visual location response.

The method may include changing, by the location response unit, any parameter of the location response based on the ambient condition.

The method may include changing, by the location response unit, any parameter of the location response based on a time of the location request.

The method may include selecting, by the location response unit, a type of location response based on the ambient condition.

The ambient condition may be sound.

The method may include sensing, by the location response unit, noise that exceeds a threshold and outputting a visual location response instead of an audio location response.

The method may include sensing, by the location response unit, noise that exceeds a threshold and outputting a location response that may be aimed to another device instead of an audio location response.

The ambient condition may be electromagnetic interferences.

The method may include sensing, by the location response unit, electromagnetic interferences that exceeds a threshold and outputting a visual location response instead of a location response that may be aimed to another device.

The method may include sensing, by the location response unit, electromagnetic interferences that exceeds a threshold and outputting an audio location response instead of a location response that may be aimed to another device.

The method may include retrieving, by the defibrillator, receive health information about the patient; and to configure the circuitry according to the health information.

The method may include receiving, by a receiver of the location response unit, a location request that may include the health information.

The method may include receiving, by a receiver of the location response unit, a location request that may be not included in the health information.

The method may include transmitting, by the location response unit, an alert to a predefined third party about an occurrence of a life threatening cardiac event of the patient.

The method may include detecting, by the location response unit, the location request by finding a dedicated sequence signal included in the location request.

The method may include receiving, by a receiver of the location response unit, the location request over a carrier frequency that may be allocated to an emergency service.

The method may include receiving the location response by another device; feeding, by the other device, the location response to a navigation application; and displaying, navigation information for guiding a person towards the defibrillator.

The navigation information may be inter-building navigation information.

The navigation information may be outer-building navigation information.

There may be provided a computer program product that may store instructions for receiving a location request, by a receiver of location device that may be associated with a defibrillator; and generating, by a location response unit of the location device, a location response that may be indicative of a location of the defibrillator, wherein the defibrillator may include circuitry for supplying a dose of electric current to a heart of a patient.

The computer program product may store instructions for sending, by the location response unit, a location response that may include instructions for finding the defibrillator.

The computer program product may store instructions for sending, by the location response unit, a location response that may include an indication of the location of the defibrillator.

The computer program product may store instructions for sending, by the location response unit, a location response that may include coordinates of the defibrillator.

The computer program product may store instructions for sending, by the location response unit, a location response that may include a location of an object that may be nearby the defibrillator.

The computer program product may store instructions for generating, by the location response unit, a location response that may be perceivable to a human only within a predefined range from the defibrillator.

The predefined range may be ten meters.

The predefined range may be one hundred meters.

The computer program product may store instructions for sensing, by a sensor of the location response unit, an ambient condition; and selecting, by the location response unit, the location response based on the ambient condition sensed by the sensor.

The ambient condition may be light.

The computer program product may store instructions for sensing, by the location response unit, daylight that exceeds a threshold and outputting an audio location response instead of a visual location response.

The computer program product may store instructions for sensing, by the location response unit, daylight that exceeds a threshold and outputting a location response that may be aimed to another device instead of a visual location response.

The computer program product may store instructions for changing, by the location response unit, any parameter of the location response based on the ambient condition.

The computer program product may store instructions for changing, by the location response unit, any parameter of the location response based on a time of the location request.

The computer program product may store instructions for selecting, by the location response unit, a type of location response based on the ambient condition.

The ambient condition may be sound.

The computer program product may store instructions for sensing, by the location response unit, noise that exceeds a threshold and outputting a visual location response instead of an audio location response.

The computer program product may store instructions for sensing, by the location response unit, noise that exceeds a threshold and outputting a location response that may be aimed to another device instead of an audio location response.

The ambient condition may be electromagnetic interferences.

The computer program product may store instructions for sensing, by the location response unit, electromagnetic interferences that exceeds a threshold and outputting a visual location response instead of a location response that may be aimed to another device.

The computer program product may store instructions for sensing, by the location response unit, electromagnetic interferences that exceeds a threshold and outputting an audio location response instead of a location response that may be aimed to another device.

The computer program product may store instructions for retrieving, by the defibrillator, receive health information about the patient; and to configure the circuitry according to the health information.

The computer program product may store instructions for receiving, by a receiver of the location response unit, a location request that may include the health information.

The computer program product may store instructions for receiving, by a receiver of the location response unit, a location request that may be not included in the health information.

The computer program product may store instructions for transmitting, by the location response unit, an alert to a predefined third party about an occurrence of a life threatening cardiac event of the patient.

The computer program product may store instructions for detecting, by the location response unit, the location request by finding a dedicated sequence signal included in the location request.

The computer program product may store instructions for receiving, by a receiver of the location response unit, the location request over a carrier frequency that may be allocated to an emergency service.

The computer program product may store instructions for receiving the location response by another device; feeding, by the other device, the location response to a navigation application; and displaying, navigation information for guiding a person towards the defibrillator.

The navigation information may be inter-building navigation information.

The navigation information may be outer-building navigation information.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE FIGURES

Figure 1:
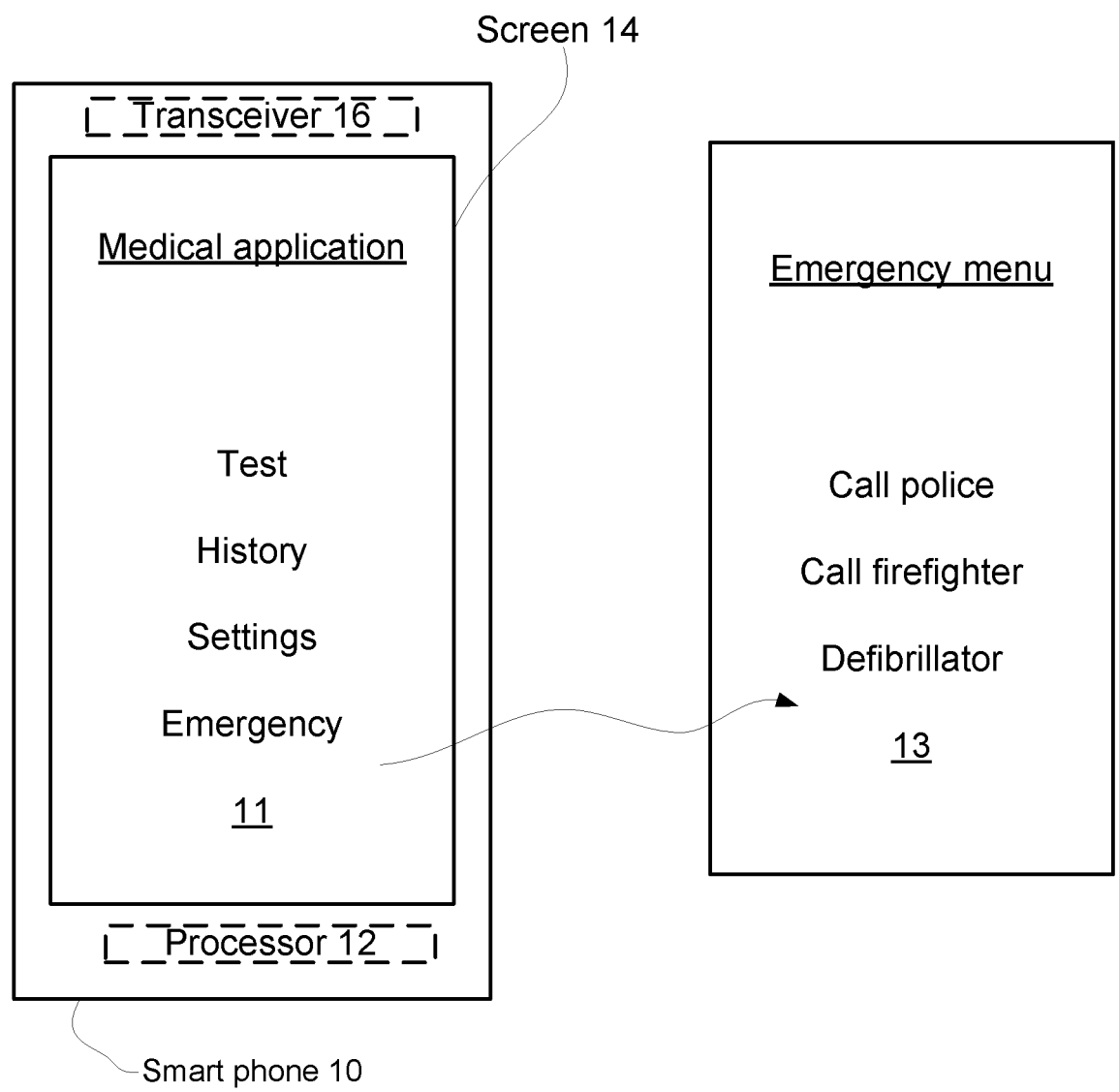
FIG. 1 illustrates a smart phone according to an embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method.

Any reference in the specification to a system should be applied mutatis mutandis to a method that may be executed by the system.

There is provided a system and method for locating a defibrillator.

The defibrillator can be equipped with a location device that may include a receiver for receiving a location request and a location response unit for generating a location response.

The location request can be generated by a requesting device.

The requesting device may be a mobile device or a stationary device. For example—the requesting device can be a combination of an interface and a transmitter, a mobile phone, a smartphone, a smart wrist, a smart watch, or any other wearable computer and/or wearable transmitter, and the like.

One or more requesting devices may be positioned around the defibrillator, at different distances from the defibrillator, at different angles in relation to the defibrillator, at paths (such as corridors) that lead to the defibrillator, and the like. For example, a requesting device may be positioned at any level of a multi-story shopping mall, near entrances of the shopping mall, near stairways and/or elevator or other noticeable objects.

When the requesting device is a computerized device then it may execute an application (or any other software) that will allow a user to trigger the generation and/or transmission of the location request. The application may be dedicated solely for the locating of the defibrillator or may also be used for other purposes (for example—the application may manage other emergency scenarios) and the like.

For example—a smart phone may execute an application that will cause the smartphone to display a symbol, sign, icon, text, image, knob, and/or virtual button that once pressed will cause the smart phone to generate and transmit the location request.

Additionally or alternatively, the smart phone may be instructed by the user (or requested by the user) to generate and transmit the location request using voice recognition and/or gesture recognition and/or tapping recognition and/or three-dimensional hologram based commands.

Additionally or alternatively, the requesting device may include a dedicated button or interface for requesting the requesting device to generate and transmit the location request.

An emergency button or any other dedicated hardware components may be attached to and/or mechanically coupled to a smart phone (or any other type of requesting device—especially a general purpose requesting device) and used to trigger the generation and transmission of the location request.

The dedicated button and/or interface may be included in a jacket that at least partially surrounds a smartphone. For example—the jacket may be the jacket illustrated in U.S. provisional patent Ser. No. 62/378,694 filing date Aug. 24, 2016 and in PCT patent application PCT/IL2017/050939—both being incorporated herein by reference.

The location device and/or any part of the location device (for example—the location response unit, the receiver) may be attached to the defibrillator, may be located within an enclosure of the defibrillator, and/or may be located in proximity (for example—within few meters) to the defibrillator. The few meters may be less than 2, 3, 4, 5, 6, 7, 8,9, 10, and even 20 meters.

The location request can be provided to the receiver via wired and/or wireless networks. Non-limiting examples of wireless networks include ZigBee, Bluetooth, Wi-Fi, BLE, IR wireless networks and the like. Non-limiting example of wired networks include power line networks, Ethernet, optical communication networks and the like.

The location request may be transmitted over a carrier frequency (or carrier frequencies) that may or may not be allocated to emergency services. For example—433 MHz., 866 MHz or any other carrier frequency. The location request can be conveyed over a light wave, over a sound wave, over an infrared wave, a radio frequency, or any electromagnetic wave of waves.

The location request may include a dedicated sequence of bits and/or symbols or any other transmitted signal that will be recognized by the location device and trigger the generation of a location response. The dedicated sequence may be determined in advance in any manner and programmed to the location unit and any device that is arranged to send a location request.

The location response may be a human perceivable response (audio signal, visual signal, audio-visual signal, acoustic signal, and the like), and/or may be a location response that may be received by another device. The location response that may be received by another device may be conveyed over a radio frequency channel or over any wired or wireless channel.

The location response may at least one of the following (or a combination of at least one of the following):

a. An audio signal that can be heard within a first predefined distance (for example between 10 meters and more than a hundred meters). The first predefined distance may be determined during a configuration and/or the manufacturing of the location device. The strength of the audio signal may be set to match the first predefined distance. For example—assuming that a human hears audio signals of a certain intensity, and assuming a certain environment (open environment, in-building environment) of a certain attenuation then the audio signal should be of a strength that will, after being attenuated by the certain attenuation, will reach the first predefined distance having about the certain intensity. The certain intensity may be determined based on hearing statistics, and the like. The strength and even the content of the audio signal (siren, repetitively changing signal, monotonic signal, audio signal that includes content) may be set in advance, may be determined based on successes or failures to hear certain audio signals, and the like. Yet for another example—the audio signal should be distinguishable from its surrounding—and the content of the audio signal may be determined or selected based on typical sounds that are located at the vicinity of the defibrillator—the typical sound may be known in advance, learnt during a learning period and the like. A user may select a content of the audio alert our of a set of different audio signals.

b. A visual signal that can be seen within a second predefined distance (for example between 10 meters and more than a hundred meters). The second predefined distance may be determined during a configuration and/or the manufacturing of the location device. The strength of the visual signal may be set to match the second predefined distance. For example—assuming that a human can see visual signals of a certain intensity, and assuming a certain environment (open environment, in-building environment) of a certain attenuation then the visual signal should be of a strength that will, after being attenuated by the certain attenuation, will reach the second predefined distance having about the certain intensity. The certain intensity may be determined based on statistics related to human vision, and the like. The strength and even the content of the visual signal (lasers beams, repetitively changing signal, static light signal, visual signal that includes content) may be set in advance, may be determined based on successes or failures to see certain audio signals, and the like. Yet for another example—the visual signal should be distinguishable from its surrounding—and the content of the visual signal may be determined or selected based on typical visual signals that are located at the vicinity of the defibrillator—the typical visual signals may be known in advance, learnt during a learning period and the like. A user may select a content of the visual alert our of a set of different visual signals of different color and/or visual symbols.

c. An electromagnetic signal (radio frequency, infrared, light, or any other electromagnetic signal) that can be sent, directly and/or indirectly via a wired and/or wireless network to another device thereby causing the other device (or yet a further device) to generate a human perceivable response.

The location response may (or may not) include instructions for finding the defibrillator. For example—the location response may provide indication of the location of the defibrillator—the indication may be coordinates, a nearby object, and the like.

The other device may feed the location response to a navigation application (such as WAZE™, GOOGLE MAPS™ and/or any inter-building and/or outdoor navigation application) that will, in turn display navigation information for guiding a person towards the defibrillator.

The location unit may be or may include an electromagnetic transmitter, and/or one or more light emitting elements (lasers and/or LEDS and/or lamps) and/or speakers (acoustic speakers, audio speakers, sirens, and the like).

The location unit may include (or may be coupled to) a sensor for sensing ambient conditions (such as a light sensor) and for selecting the location response based on the ambient conditions.

The location unit may change and/or adapt and/or select any parameter of the location response based on time, date, ambient conditions, and the like.

The location unit may select the type of location response and/or one or more parameters of the location response based on ambient conditions.

For example—when the sensor is a sound sensor (for example a microphone) and senses a noisy environment the location unit may increase the volume of an audio location response and/or select a visual response and/or a location response that is aimed to another device.

Yet for another example—when the sensor is a light sensor and it senses a strong daylight (what forms a strong daylight signal can be set in advance and/or may be dynamically changed to a certain threshold—for example the certain threshold may be set to be equal, to exceed or be lower than a certain margin than the intensity of the illumination generated by the location device) and the location unit may select a visual location response that can be seen even in strong daylight conditions and/or may select an audio response and/or a location response that is aimed to another device.

Yet for another example—when the sensor (for example the sensor is a receiver or a part of the receiver) senses strong electromagnetic interferences (what forms a electromagnetic interferences signal can be set in advance and/or may be dynamically changed to a certain threshold—it can be measured in signal to noise ratio, RSSI, and the like) then the location unit may change the modulation or any other transmission parameter of a location response that is aimed to another device—or may select an audio and/or visual response.

According to an embodiment of the invention the defibrillator can also receive information about the person that experiences the life threatening cardiac event. This information will be referred to as patient information.

The patient information may be included in the location request, may be transmitted with the location request, may be transmitted and a different time and/or a different link from the location request and the like.

The patient information can identify the person, can identify one or more attributes of the person (age, weight, size, gender . . . ) that can be used by the defibrillator, the location device, and/or any other device to retrieve health information (from an external or internal database) that may be used to configure the defibrillator (configuration may be done by a controller of the defibrillator, by a controller of the location device)—thus allowing the defibrillator to be tailored (in an optimal and/or sub-optimal manner) to the actual or expected condition of the person. In a nut shell, a larger person with more soft tissues in the chest area will require a stronger dose of energy.

The configuration may include any parameter related to the electrical current supplied by the defibrillator.

The database may be stored in one or more remote computers—such as servers of a healthcare provider, of a hospital, and the like.

According to an embodiment of the invention the defibrillator and/or the location device and/or the requesting device or any other device may also send an alert or otherwise inform (directly or indirectly—by any other device and/or network) a predefined third party (such as a hospital, an emergency health service, a firefighting service, or any other medical caretaker) about the occurrence of the life threatening cardiac event.

The alert may be set using the same communication links and/or networks used for conveying the location request and/or the location response—or may use another communication network and/or another communication link.

The notification may speed up the arrival of medical emergency service or other personnel that may provide medical services on the spot and/or evacuate the person to the hospital.

The alert can be sent when a location request is receiver and/or when a location response is generated and/or when the defibrillator is used and/or when the defibrillator is extracted from its enclosure, and/or when the location response is muted or stopped (either by a person or automatically).

FIG. 1 illustrates a smartphone 10 and two screen shots—one (left) of a main menu 11 of an application and the second the emergency menu 13—that enables to contact police, a firefighter or initiate the defibrillator location process. The smartphone 10 may include a processor 12, a screen 14 and a transceiver 16. It should be noted that the smartphone may be arranged to initiate the defibrillator location process using any other application—and while displaying any other screenshots.

Figure 2:
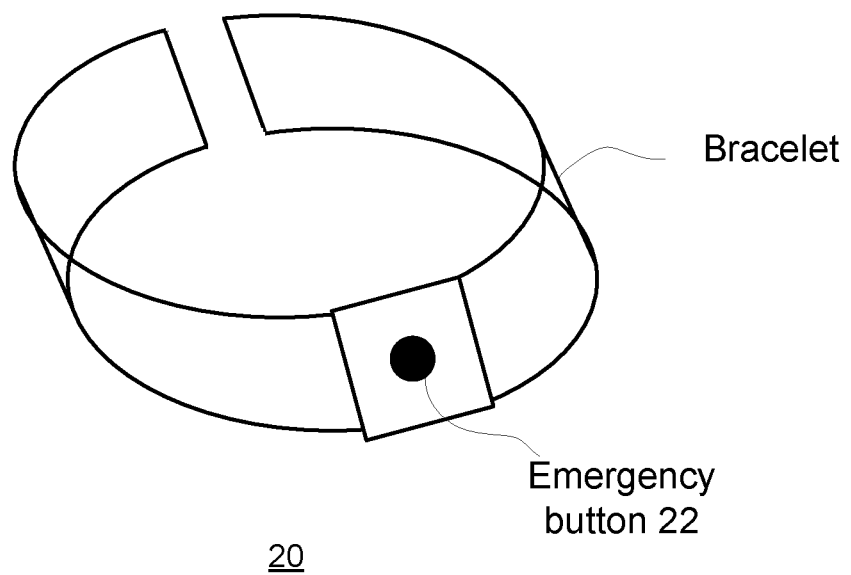
FIG. 2 illustrates a bracelet according to an embodiment of the invention

FIG. 2 illustrates a bracelet 20 with an emergency button 22 that once pressed may initiate the defibrillator location process. The emergency button can be a hardware button, or an icon displayed by the bracelet. The bracelet can be replaced by a neckless, be a part of a smart watch and the like.

Figure 3:
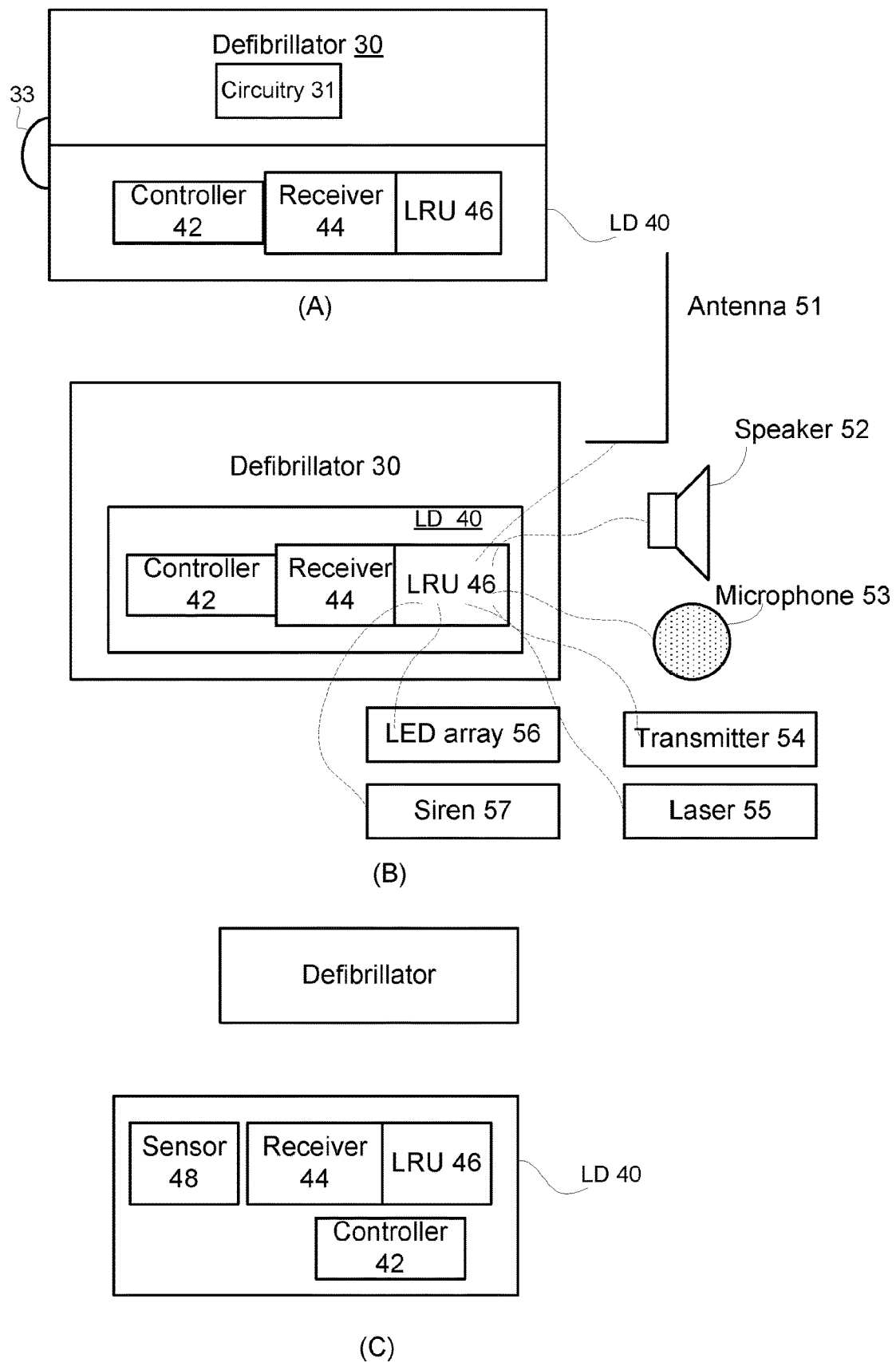
FIG. 3 illustrates defibrillators and location devices according to embodiments of the invention.

FIG. 3 illustrates:
a. (A) a location device (LD) 40 that is attached to a defibrillator 30. The LD 40 includes a controller 42 for controlling the LD, a receiver 44 for receiving the location request and a location response unit (LRU) 46 for generating the location response. The defibrillator 30 can be any defibrillator known in the art. It includes circuitry 31 for supplying a dose of electric current to a heart of a patient. The circuitry may include a current source, current regulators, leads, controller for controlling the generation and supply of the current, and the like.

b. (B) A defibrillator 30 that includes the LD 40. The LRU may include at least one of an antenna 51 (such as but not limited to an RF antenna), a speaker 52, a microphone 53, a transmitter 54 (such as but not limited to an RF transmitter), a laser transmitter 55 (for generating a visual alert and/or communication with the requesting device) a siren 57 and/or a LED array 56 that includes one or more light emitting diodes.

c. (C) A defibrillator 30 that is located in proximity of the LD 40. The LD also includes a sensor 48 for sensing ambient conditions. The sensor may be included in any LD of options (A) and (B). The receiver may act as a sensor. There may be more than one sensor of one or more types.

Figure 4:
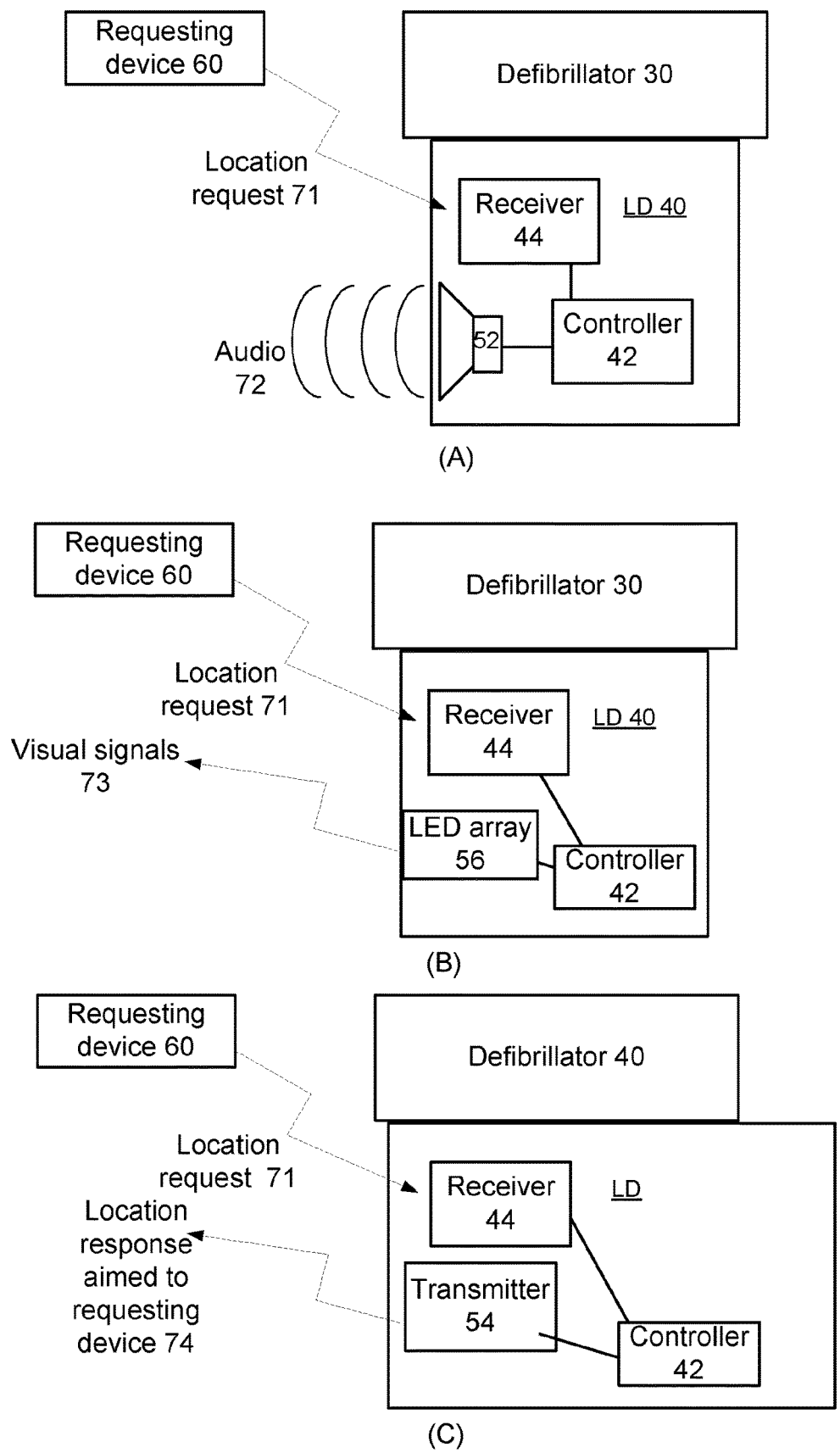
FIG. 4 illustrates defibrillators and location devices according to embodiments of the invention.

FIG. 4 illustrates:

a. (A) A requesting device 60 that transmits a location request 71, the location request is received by the receiver 44 of the LD 40, the LD 40 generates an audio alert 72 by using a speaker 52 of the LD.

b. (B) A requesting device 60 that transmits a location request 71, the location request is received by the receiver 44 of the LD 40, the LD generates a visual alert 73 by using a LED array 56.

c. (C) A requesting device 60 that transmits a location request 71, the location request is received by the receiver 44 of the LD 40, the LD generates a location response 74 that is aimed to the requesting device.

Figure 5:
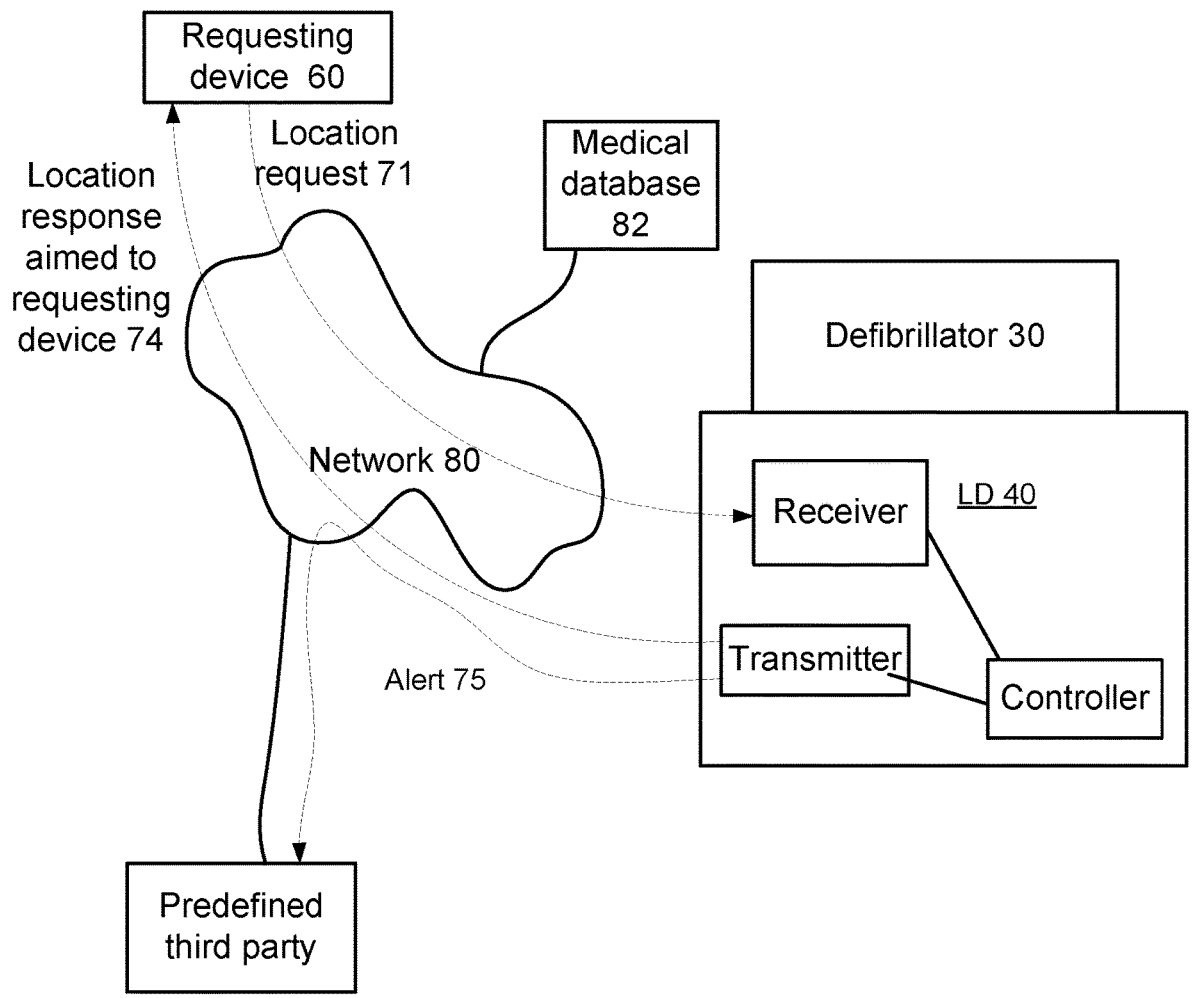
FIG. 5 illustrates a defibrillator and a location device according to an embodiment of the invention.

FIG. 5 illustrates a requesting device 60 that transmits a location request via a network 80, the location request is received by the receiver 44 of the LD 40, the LD 40 generates a location response 74 that is aimed to the requesting device and passes through the network before reaching the requesting device. FIG. 5 also shows medical data base 80 that can be accessed using patient information, and also shows an alert 75 that is sent to the predefined third party. The database 80 may be accessed by the location device 40 and/or the database 80 cna be accessed by the requesting device 60 or any other party—and the accessed data from the database 80 may be sent to the location device 40.

Figure 6:
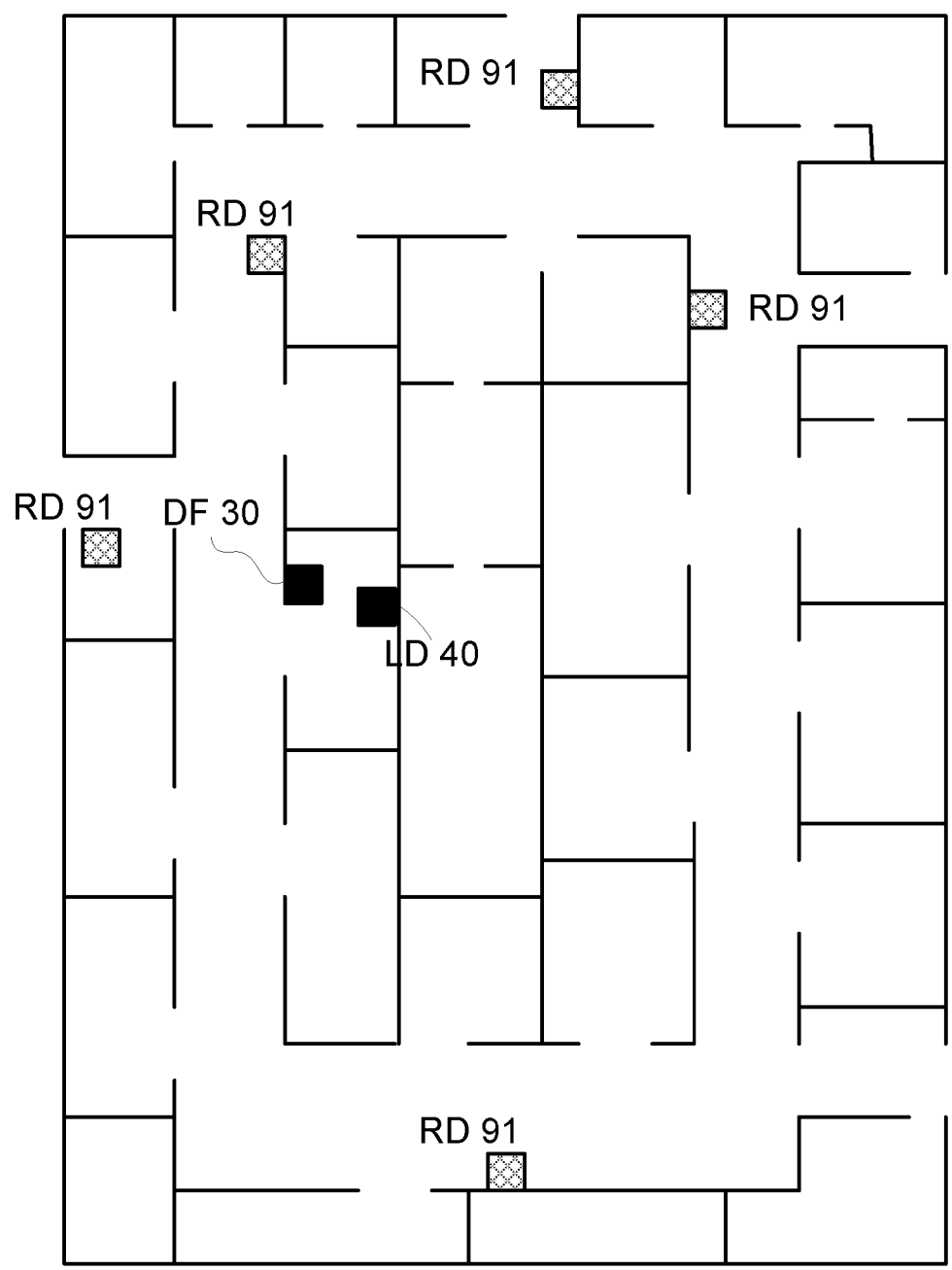
FIG. 6 illustrates a defibrillator and location devices according to embodiments of the invention.

FIG. 6 is a cross sectional view of a single level of a shopping mall. Requesting devices (RD) 91 are located in various positions and can be used to generate a location request that is aimed to the defibrillator (DF) 30 and/or the location device (LD) 40 positioned near the DF. Any other arrangements of RDs, DF 30 and LD may be provided. One or more RD may act as a relay and/or may relay location requests and/or location responses between other LRD and the LD.

Figure 7:
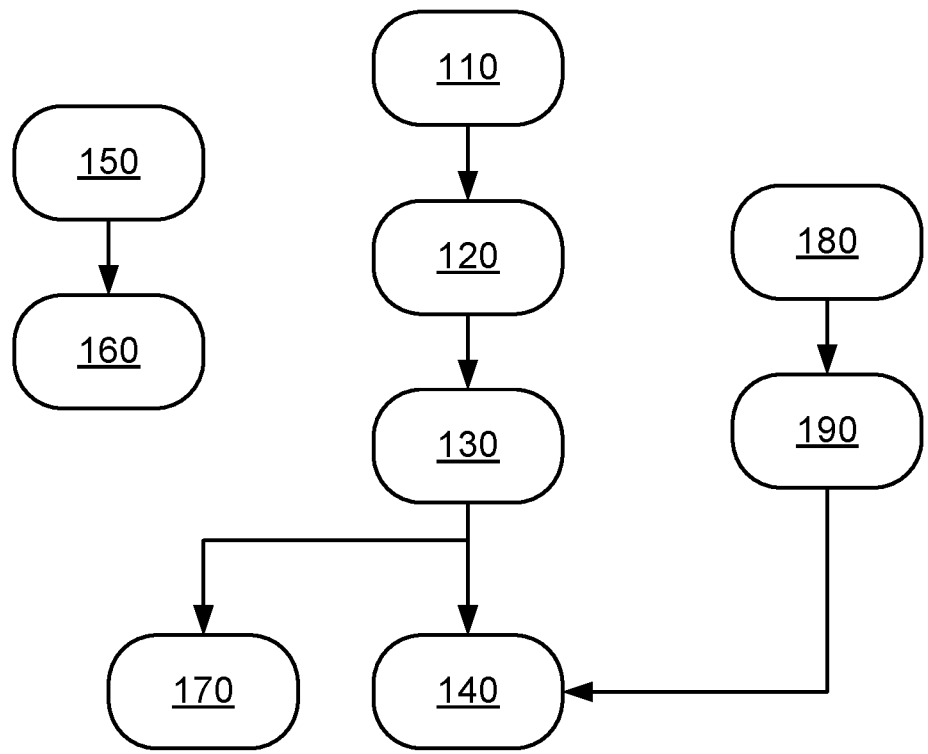
FIG. 7 illustrates a method of receiving a location via a location request.

FIG. 7 illustrates method 100.

Method 100 may include:

a. Step 110 of receiving a request to generate and transmit a location request. A user may use a requesting device (for example—the user may interact with the requesting device) to generate the request.

b. Step 120 of generating the location request and transmitting the location request.

c. Step 130 of receiving by a location device the location request.

d. Step 140 of generating a location response—in response to the reception of the location request. This may include transmitting the location response, and the like.

The method may also include step 150 receiving, by defibrillator, patient information and step 160 of configuring the defibrillator according to the patient information. This may include retrieving heath information about the person—using a person identifier.

The method may also include step 170 of sending an alert or otherwise inform a predefined third party (such as a hospital, an emergency health service, a firefighting service, or any other medical caretaker) about the occurrence of the life threatening cardiac event.

The method may include step 180 sensing an ambient condition or other condition that may affect the reception of the location response—and step 190 adjusting and/or selecting the location response accordingly.

Any reference to the term "comprising" or "having" should be interpreted also as referring to "consisting" of "essentially consisting of". For example—a method that comprises certain steps can include additional steps, can be limited to the certain steps or may include additional steps that do not materially affect the basic and novel characteristics of the method—respectively.

The invention may also be implemented in a computer program for running on a computer system, at least including code portions for performing steps of a method according to the invention when run on a programmable apparatus, such as a computer system or enabling a programmable apparatus to perform functions of a device or system according to the invention. The computer program may cause the storage system to allocate disk drives to disk drive groups.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc. A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system. The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one current or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A defibrillator comprising:
circuitry for supplying a dose of electric current to a heart of a patient; and a location device;
wherein the location device comprises a controller for controlling the location device, a receiver for receiving a location request, and a location response unit for generating a location response;
wherein the location response is indicative of a location of the defibrillator;
wherein the location response unit comprises a sensor for sensing an ambient condition; wherein the location response unit is arranged to select the location response based on the ambient condition sensed by the sensor;
wherein the ambient condition is electromagnetic interferences and wherein the location response unit is arranged to sense electromagnetic interferences that exceeds a threshold and to output a visual location response or an audio location response, wherein the visual location response or the audio location response is sent instead of a location response that is aimed to another device.

2. The defibrillator according to claim 1, wherein the location response comprises instructions for finding the defibrillator that once fed to a navigation application causes the navigation application to display navigation information for guiding a person towards the defibrillator.

3. The defibrillator according to claim 1, wherein the location response comprises an indication of the location of the defibrillator.

4. The defibrillator according to claim 1, wherein the location response comprises coordinates of the defibrillator.

5. The defibrillator according to claim 1, wherein the location response comprises a location of an object that is nearby the defibrillator.

6. The defibrillator according to claim 1, wherein the location response unit is arranged to change any parameter of the location response based on the ambient condition.

7. The defibrillator according to claim 1, wherein the location response unit is arranged to change any parameter of the location response based on a time of the location request.

8. The defibrillator according to claim 1, wherein the location response unit is arranged to select a type of location response based on the ambient condition.

9. The defibrillator according to claim 1 wherein the defibrillator is arranged to retrieve or receive health information about the patient; and to configure the circuitry according to the health information.

10. The defibrillator according to claim 1 wherein the receiver is arranged to receive the location request over a carrier frequency that is allocated to an emergency service.

11. A method for assisting in locating a defibrillator, the method comprises receiving a location request, by a receiver of location device that is associated with a defibrillator; and generating, by a location response unit of the location device, a location response that is indicative of a location of the defibrillator, wherein the defibrillator comprises circuitry for supplying a dose of electric current to a heart of a patient; wherein the location response unit comprises a sensor for sensing an ambient condition;

wherein the location response unit is arranged to select the location response based on the ambient condition sensed by the sensor; wherein the ambient condition is electromagnetic interference.

\* \* \* \* \*